(12) United States Patent
Gerhardt

(10) Patent No.: US 6,190,418 B1
(45) Date of Patent: *Feb. 20, 2001

(54) ENDOPROSTHESIS WITH ANCHORING SHAFT

(75) Inventor: Harald Gerhardt, Karlsruhe (DE)

(73) Assignee: orto Maquet GmbH & Co. KG, Rastatt (DE)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/275,160

(22) Filed: Mar. 24, 1999

(30) Foreign Application Priority Data

Mar. 24, 1998 (DE) .......................... 298 05 344 U

(51) Int. Cl.⁷ ...................................... A61F 2/32
(52) U.S. Cl. .......................................... 623/23.31
(58) Field of Search ................... 623/23, 16, 18, 623/20, 22; 606/86, 79, 80

(56) References Cited

U.S. PATENT DOCUMENTS 5,549,705 * 8/1996 Michielli et al. ..................... 623/23

FOREIGN PATENT DOCUMENTS

| 8213101 | 8/1982 | (DE) | ................. A61F/1/03 |
| 8318360 | 9/1985 | (DE) | ................. A61F/2/28 |
| 3822153 | 3/1989 | (DE) | ................. A61F/2/36 |
| 3740438 | 6/1989 | (DE) | ................. A61F/2/30 |

* cited by examiner

Primary Examiner—David J. Isabella
(74) Attorney, Agent, or Firm—McCormick, Paulding & Huber LLP

(57) ABSTRACT

In a long bone endoprosthesis, the anchoring shaft on at least a part of its length has a cross section of generally rectangular or other polygonal shape and with rounded corners and straight side sections allowing the anchoring shaft to fit more closely with the bone when the anchoring shaft is inserted into a bone recess cut with a rotary cutting head having a minimum radius, the rounded corners of the anchoring shaft having radii equal to or greater than the minimum radius of the cutter head.

6 Claims, 2 Drawing Sheets

ENDOPROSTHESIS WITH ANCHORING SHAFT

FIELD OF THE INVENTION

The invention concerns an endoprosthesis with an anchoring shaft, which is intended for use in a recess produced in a long bone, wherein the anchoring shaft has a cross section that is at least approximately polygonal on at least one part of its length.

BACKGROUND OF THE INVENTION

An example of this type of endoprosthesis is the part of an artificial hip joint that is used in the femur and is supposed to replace the head and neck of the femur. To seat the prosthesis firmly in the bone, the recess for the shaft must be precisely machined according to the anchoring philosophy ("formfit" or "pressfit"). In practice, it is not possible to produce the recess in the bone so precisely that the desired seat is achieved along the whole peripheral surface of the shaft.

Therefore, a new procedure is now being used in practice in which the recess is cut out using a program-controlled robot. This makes it possible to produce the recess with high precision.

However, when today's usual straight shaft prostheses, which frequently have a rectangular cross section to achieve rotational stability, are used, the problem is that no corners can be cut with a rotary cutting head. This is mainly due to the fact that the cutting head cannot have less than a certain minimum radius for reasons of stability. The cutting head is on a relatively long shaft and its diameter must be greater than the shaft diameter, so that the shaft can follow the cutting head into the recess. If the shaft diameter is too small, the shaft bends in the lateral forces, so the desired precision cannot be achieved. As a rule, the minimum cutting head radius is therefore approximately 5 mm.

If the bone is allowed to stand in the corners corresponding to the radius of the cutting head, there is a risk that the bone will split when the prosthesis is inserted with its sharp square edges. On the other hand, if the corners are completely cut out, there are hollow spaces on both sides of the corner line, in which the prosthesis shaft is not adjacent to the bone and in which not only does the prosthesis have no stop, but there is also a danger that the bone will recede there, since there is no stress on it.

The problem of the invention is to produce an endoprosthesis of the type mentioned at the beginning so that the shaft can lie on the wall of the recess on at least part of its length with its entire peripheral surface.

SUMMARY OF THE INVENTION

The invention solves this problem by having the cross sectional outline of the shaft composed of straight and curved line sections and having the minimum radius of curvature of the curved line sections always be larger than or equal to the radius of a cutting head used to produce the recess in the bone. This eliminates the danger that either hollow spaces are created in the corner areas between straight line sections or splitting forces are exerted on the bone by sharp edges of the prosthesis shaft.

In the preferred form of embodiment, the cross section of the shaft is basically rectangular on at least part of its length, and the midpoint of the curve of the curved line section in the corner areas lies on the respective median line of two side lines contiguous one another.

The curved line section must therefore not transition tangentially into the respective straight line section or lateral surfaces of the shaft. Rather, the respective curvature midpoint on the median line can also be shifted so that the corresponding curved line runs through the intersection of the two straight side lines contiguous to one another or even outside them.

A curved line section can also consist of several subsections with different radii of curvature. A curved line section can also consist of curved subsections whose curvature midpoints are some distance apart.

Another design possibility is that the distances of the curvature midpoint of a curved line section be different from the side lines connected by them, i.e., that the respective curvature midpoint not lie on the median line between the two side lines contiguous to one another.

Basically, the hold of the shaft in the bone is improved the greater the contact surface between the shaft and the bone is. This contact surface can be enlarged by providing—seen in cross section—in the area of at least one side line, an additional curved line section, whose radius of curvature is not smaller than the minimum radius of curvature.

BRIEF DESCRIPTION OF THE DRAWINGS

Other features and advantages of the invention will emerge from the following description, which explains the invention in connection with the enclosed drawings and the examples of embodiment.

DETAILED DESCRIPTION OF THE PREFERRED EMBODIMENT

Figure 1:
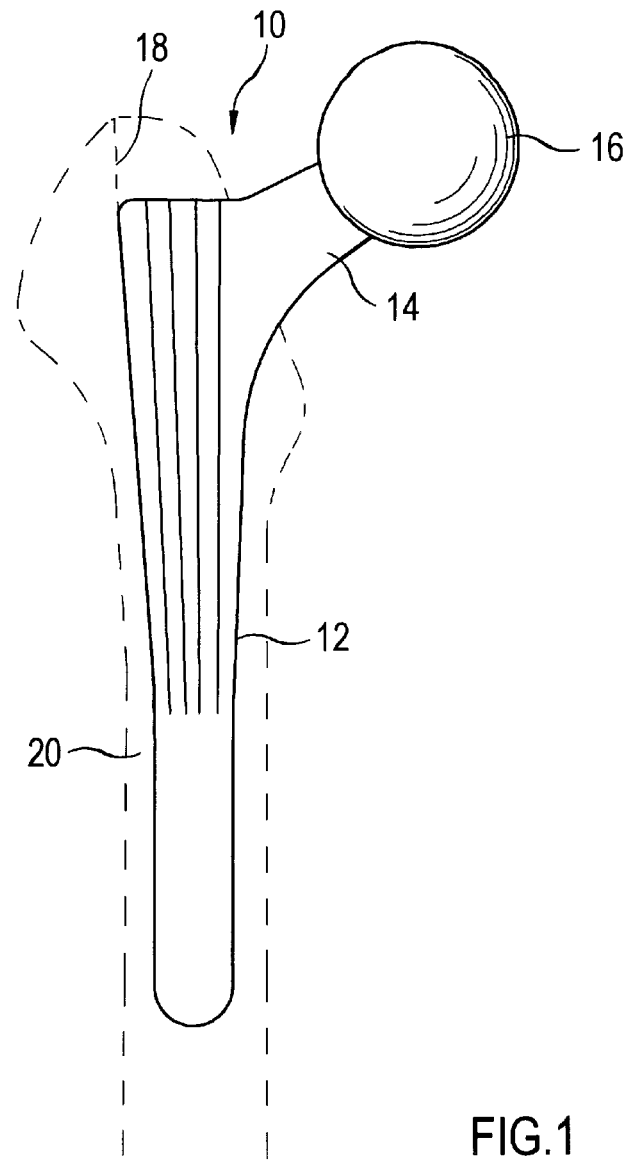
FIG. 1 shows a schematic side view of part of an artificial hip joint to be anchored in a femoral bone.
Figure 2:
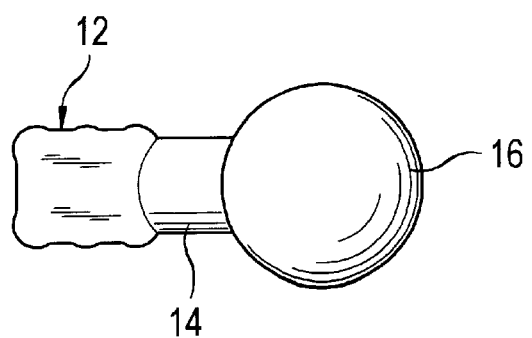
FIG. 2 shows a schematic top view of the prosthesis part shown in FIG. 1.

The endoprosthesis 10 shown in FIG. 1 is part of an artificial hip joint and includes a shaft 12, which is connected on its upper end to an appendix 14 that replaces the neck of the femur and projects laterally and that has a ball joint 16 replacing the head of the femur. The shaft 12 is inserted into a recess 18 which was cut in a femoral bone 20 shown in dashes. The shaft 12 has, at least in its upper area near the appendix 14, a basically rectangular cross section (FIG. 2) and tapers toward its lower end. The shape of the cross section in the upper section of the shaft on which the major forces are exerted, which is very important for seating the prosthesis 10 in the bone 20, will now be explained in greater detail using FIGS. 3 to 5.

Figure 3:
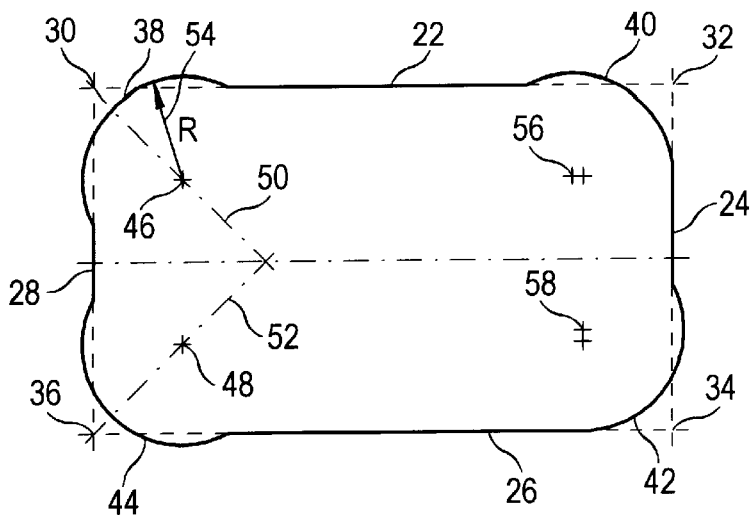
FIGS. 3 to 5 show idealized cross sections through various forms of embodiment of the shaft of the prosthesis part shown in FIGS. 1 and 2 without considering the artificial neck of the femur.

The shaft cross section shown in FIG. 3 is basically rectangular with sides or straight line sections 22, 24, 26 and 28 at right angles to one another, wherein the unbroken parts of these straight lines reflect the actual contours, while the broken sections complete the rectangle up to the mathematical corners 30, 32, 34 and 36. In the corner areas, the straight line sections 22 to 28 are connected to one another by curved line sections 38, 40, 42 and 44.

The two curved line sections 38 and 44 are formed by an arc around a midpoint 46 and 48. The midpoints 46, 48 are on a median line 50 and 52 between rectangle sides 22 and 28 next to one another in one case and 26 and 28 in the other case. The radius 54 of this arc is greater than the respective distance of the midpoint 46 or 48 from the rectangle sides 22, 28 and 26, 28. In this way, the arcs 38 and 44 do not transition tangentially into the respective side lines 22 and 28 and 26 and 28, but form similar corner bulges on the shaft.

The curved sections 40 and 42 on corners 32 and 34 are also formed by arcs, but their midpoint 56 or 58 is not on the median line between sides 22 and 24 or 24 and 26, and it is laterally offset from it, so that arc 40 transitions tangentially into side 24 and arc 42 tangentially into side 26, as can be seen from FIG. 3, while arcs 40, 44 project like bulges beyond the other sides 22 and 24.

The corner areas of the shaft can be designed differently or the same as shown in FIG. 3.

Figure 4:
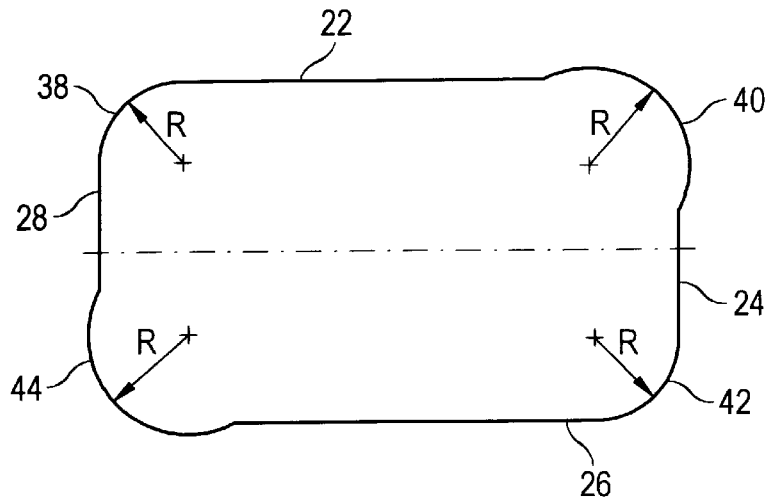

In the form of embodiment in FIG. 4, the parts that correspond to one another have the same reference numbers as in FIG. 3. In the form of embodiment in FIG. 4, the curved line or contour sections 38 and 42 have a smaller radius of curvature than curved line sections 40, 44. Thus, the radius of curvature need not be equal in all the corner areas. It must only not be smaller than the minimum possible radius of the cutter used for hollowing out the bone.

Figure 5:
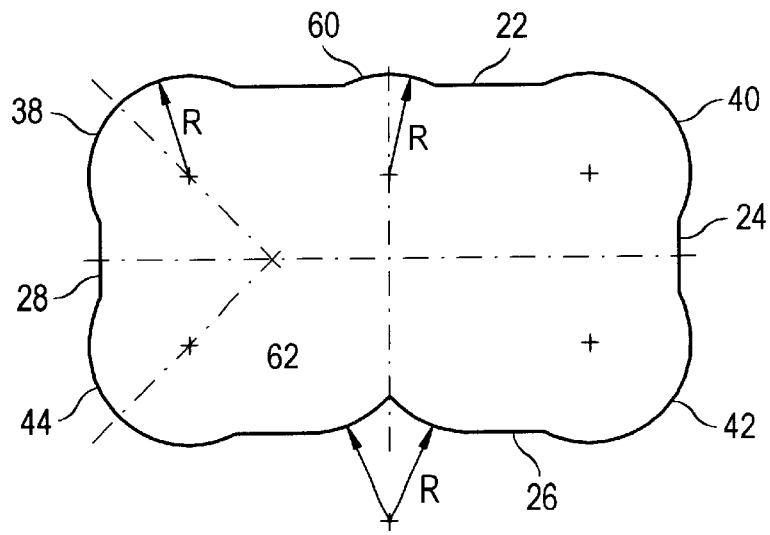

The example of embodiment in FIG. 5, in which the corresponding parts are also marked with the same reference numbers as in FIG. 3, is different from the example of embodiment shown in FIG. 3 mainly because of the fact that the curved contour sections in the corner areas 30, 32, 34 and 36 are composed of sections with a different radius of curvature and by the fact that within the longitudinal sides 22 and 24 of the cross sectional contour, there are other curved sections 60 and 62, to whose radius of curvature the same conditions apply as for the respective radius of curvature in the corner areas of the shaft. As can be seen in FIG. 5, curved section 62 is composed of two intersecting arc sections, but the tip created thereby in the contours is pointed toward the inside of the cross sectional contour, so that the complementary form in the knee can be cut with no problem with a rotary cutter. With these additional bulges and curved sections, the contact surfaces between the shaft and the wall of the recess are enlarged, and the rotational stability of the shaft in the knee is therefore increased.

The examples of embodiment above show that the recess for the respective cross section of the shaft can be cut out using a cutting head so that the shaft surface can be adjacent to the bone wall surrounding the recess in all areas. This seats the shaft well in the bone right away and encourages the prosthesis to grow into the bone.

What is claimed is:

1. An endoprosthesis to be implanted in a prepared recess in a long bone, the recess having a polygonal cross section including straight and curved segments, said endoprosthesis comprising an elongated anchoring shaft having at least a portion thereof exhibiting a polygonal cross section substantially matching the prepared recess;

said polygonal cross section including corners and an equal number of sides each of which sides has at least one straight segment, at least one of said straight segments of at least two sides, respectively, merging toward at lest one of said corners, said at least one of said corners being a curved segment having a radius of curvature and a center of curvature located at an intersection of two lines parallel to said merging straight segments, said two lines being respectively spaced from said merging straight segments by a distance less than said radius of curvature such that said at least one corner extends outwardly from said merging straight segments of said polygonal cross section.

2. The endoprosthesis of claim 1 wherein said polygonal cross section is substantially rectangular defining four corners and four sides.

3. The endoprosthesis of claim 1 wherein said at least one curved segment includes varied arcuate subsegments having different radii of curvature.

4. The endoprosthesis of claim 1 wherein said at least one curved segment includes varied arcuate subsegments wherein each of said subsegments defines an arc midpoint.

5. The endoprosthesis of claim 1 wherein said at least one curved segment connects two of said straight segments, said at least one curved segment defining a curvature midpoint that is spaced at different distances from said two of said straight segments.

6. The endoprosthesis of claim 1 wherein at least one straight segment between adjacent corners contains a curved segment.

* * * * *

UNITED STATES PATENT AND TRADEMARK OFFICE
CERTIFICATE OF CORRECTION

PATENT NO. : 6,190,418 B1
DATED : February 20, 2001
INVENTOR(S) : Harald Gerhardt It is certified that error appears in the above-identified patent and that said Letters Patent is hereby corrected as shown below:

<u>Column 4,</u>
Line 17, after "toward at", delete "lest" and insert -- least --.

Signed and Sealed this

Thirtieth Day of October, 2001

Attest:

*Attesting Officer*

NICHOLAS P. GODICI
*Acting Director of the United States Patent and Trademark Office*